(12) United States Patent
Pardonge

(10) Patent No.: US 9,889,263 B2
(45) Date of Patent: Feb. 13, 2018

(54) FLUID DISPENSER DEVICE

(75) Inventor: Jean-Marc Pardonge, Les Authieux sur Port St Ouen (FR)

(73) Assignee: APTAR FRANCE SAS, Le Neubourg (FR)

( * ) Notice: Subject to any disclaimer, the term of this patent is extended or adjusted under 35 U.S.C. 154(b) by 775 days.

(21) Appl. No.: 13/697,267

(22) PCT Filed: Jun. 9, 2011

(86) PCT No.: PCT/FR2011/051314
§ 371 (c)(1),
(2), (4) Date: Jan. 15, 2013

(87) PCT Pub. No.: WO2011/154660
PCT Pub. Date: Dec. 15, 2011

(65) Prior Publication Data
US 2013/0133652 A1    May 30, 2013

(30) Foreign Application Priority Data

Jun. 11, 2010 (FR) ...................... 10 54634

(51) Int. Cl.
*A61M 15/00* (2006.01)

(52) U.S. Cl.
CPC .......... *A61M 15/00* (2013.01); *A61M 15/004* (2014.02); *A61M 15/0008* (2014.02);
(Continued)

(58) Field of Classification Search
CPC .............. A61M 15/00; A61M 15/0028; A61M 15/033–15/0041; A61M 15/0043;
(Continued)

(56) References Cited

U.S. PATENT DOCUMENTS

2002/0078951 A1\* 6/2002 Nichols et al. .......... 128/200.22
2008/0041368 A1\* 2/2008 Jones et al. .............. 128/200.23
(Continued)

FOREIGN PATENT DOCUMENTS

EP    2 011 536 A1    1/2009
FR    2 909 644 A1    6/2008
(Continued)

OTHER PUBLICATIONS

International Preliminary Report on Patentability for PCT/FR2011/051314.

*Primary Examiner* — Todd J Scherbel
*Assistant Examiner* — Ned T Heffner
(74) *Attorney, Agent, or Firm* — Sughrue Mion, PLLC

(57) ABSTRACT

A fluid dispenser device including a body, an elongate flexible strip supporting a plurality of reservoirs, each containing a dose of fluid or powder; an reservoir-opening mechanism for opening a reservoir on actuation; a first displacement mechanism for causing the flexible strip to advance before, during and/or after actuation, so as to bring a full reservoir into register with the reservoir-opening mechanism; and a second displacement mechanism for displacing a full reservoir against the opening mechanism each actuation. The leading end of the flexible strip is fastened to a rotary receiver element, the receiver element including a set of peripheral teeth that co-operates with a movable traction member, a stressed spring acting on the movable traction member so as to displace it, the displacement of the movable traction member causing the receiver element to turn, such that the receiver element exerts a traction force on the elongate strip.

12 Claims, 2 Drawing Sheets

(52) U.S. Cl.
CPC .... *A61M 15/0026* (2014.02); *A61M 15/0033* (2014.02); *A61M 15/0036* (2014.02); *A61M 15/0041* (2014.02); *A61M 15/0045* (2013.01); *A61M 15/0051* (2014.02); *A61M 15/0055* (2014.02); *A61M 15/0091* (2013.01); *A61M 15/0096* (2014.02); *A61M 2202/064* (2013.01)

(58) Field of Classification Search
CPC .......... A61M 15/0045; A61M 15/0051; A61M 15/0055; A61M 15/0056; A61M 15/0065; A61M 15/0091; A61M 2015/0048; A61M 2202/064

See application file for complete search history.

(56) References Cited

U.S. PATENT DOCUMENTS

| | | | |
|---|---|---|---|
| 2008/0099015 A1* | 5/2008 | Pocock ............. | A61M 15/0045 128/203.15 |
| 2009/0188498 A1* | 7/2009 | Thoemmes et al. ..... | 128/203.21 |
| 2010/0012119 A1 | 1/2010 | Sallak et al. | |
| 2010/0258120 A1 | 10/2010 | Colomb | |
| 2010/0319693 A1 | 12/2010 | Fagot et al. | |
| 2011/0048419 A1 | 3/2011 | Kirniak | |

FOREIGN PATENT DOCUMENTS

| | | |
|---|---|---|
| FR | 2 930 163 A1 | 10/2009 |
| WO | 2008/081132 A2 | 7/2008 |
| WO | 2009/077697 A1 | 6/2009 |

* cited by examiner

FLUID DISPENSER DEVICE

CROSS REFERENCE TO RELATED APPLICATIONS

This application is a National Stage of International Application No. PCT/FR2011/051314 filed Jun. 9, 2011, claiming priority based on French Patent Application No. 1054634, filed Jun. 11, 2010, the contents of all of which are incorporated herein by reference in their entirety.

The present invention relates to a fluid dispenser device, and more particularly to a dry-powder inhaler.

Inhalers are well known in the prior art. Various types exist. A first type of inhaler contains a reservoir receiving many doses of powder, the inhaler being provided with metering means making it possible, on each actuation, to remove one dose of said powder from the reservoir, so as to bring said dose into an expulsion duct in order to be dispensed to the user. Inhalers including individual reservoirs, such as capsules, that are loaded into the inhaler just before said reservoir is used are also described in the prior art. The advantage of such devices is that it is not necessary to store all of the doses inside the appliance, such that said appliance can be compact. However, the inhaler is more difficult to use, since the user is obliged to load a capsule into the inhaler before each use. Another type of inhaler consists in placing the doses of powder in individual predosed reservoirs, then in opening one of the reservoirs each time the inhaler is actuated. That implementation seals the powder more effectively since each dose is opened only when it is about to be expelled. In order to make such individual reservoirs, various techniques have already been proposed, such as an elongate blister strip or blisters disposed on a rotary circular disk. All existing types of inhalers, including those described above, present both advantages and drawbacks associated with their structures and with their types of operation. Thus, with certain inhalers, there is the problem of metering accuracy and reproducibility on each actuation. In addition, the effectiveness of the dispensing, i.e. the fraction of the dose that effectively penetrates into the user's lungs in order to have a beneficial therapeutic effect, is also a problem that exists with a certain number of inhalers. A solution for solving that specific problem has been to synchronize the expulsion of the dose with the inhalation of the patient. Once again, that can create drawbacks, in particular in that type of device, the dose is generally loaded into an expulsion duct before inhalation, then expulsion is synchronized with inhalation. That means that if the user drops, shakes, or manipulates the inhaler in an undesirable or inappropriate manner between the moment when the user loads the dose (either from a multidose reservoir or from an individual reservoir) and the moment when the user inhales, then the user risks losing all or part of the dose, with said dose possibly being spread about inside the appliance. In that event, there can exist a high risk of overdosing the next time the device is used. The user who realizes that the dose is not complete will load a new dose into the appliance, and while the new dose is being inhaled, a fraction of the previous dose that was lost in the appliance could thus be expelled at the same time as the new dose, thereby causing an overdose. In the treatments envisaged, such overdosing can be very harmful, and the authorities in all countries are issuing ever-stricter requirements to limit the risk of overdosing as much as possible. With regard to opening the individual reservoirs, it has been proposed to peel off or to unstick the closure layer. That presents the drawback of difficulty in controlling the forces to be applied in order to guarantee complete opening, without running the risk of opening the next reservoir, particularly if the opening means need to be actuated by inhalation. Another problem that exists with inhalers provided with blister strips is associated with the displacement of the strip, and with storage of the used portion of the strip. Thus, depending on the length of the strip and/or the thickness of the blisters, a large amount of space can turn out to be necessary, and any blockage of the blister strip can prevent the inhaler from functioning properly. In addition, when the device for advancing the strip pulls simultaneously on the leading end of the strip so as to avoid poor rolling up, a problem can occur over successive actuations, in particular because the rolled-up diameter of the used strip increases progressively.

An object of the present invention is to provide a fluid dispenser device, in particular a dry-powder inhaler, that does not have the above-mentioned drawbacks.

In particular, an object of the present invention is to provide such an inhaler that is simple and inexpensive to manufacture and to assemble, that is reliable in use, guaranteeing metering accuracy and metering reproducibility on each actuation, providing an optimum yield with regard to the effectiveness of the treatment, by making it possible to dispense a substantial fraction of the dose to the zones to be treated, in particular the lungs, avoiding, in safe and effective manner, any risk of overdosing, and that is as compact as possible, while guaranteeing sealing and absolute integrity of all of the doses up to their expulsion.

Another object of the present invention is to provide such an inhaler provided with a blister strip, in which inhaler, storage of the used strip portion is optimized, and the risk of the strip blocking is minimized.

The present invention thus provides a fluid dispenser device comprising a body, said device further comprising: an elongate flexible strip supporting a plurality of reservoirs, each containing a dose of fluid or powder; reservoir-opening means for opening a respective reservoir on each actuation; first displacement means for causing said flexible strip to advance before and/or during and/or after each actuation, so as to bring a full reservoir into register with said reservoir-opening means; and second displacement means for displacing a full reservoir against said opening means each time the device is actuated, the leading end of said flexible strip, in the advance direction of said strip, being fastened to a rotary receiver element, said device being characterized in that said receiver element includes a set of peripheral teeth that co-operates with a movable traction member, a stressed spring acting on said movable traction member so as to displace it, the displacement of said movable traction member causing said receiver element to turn, such that said receiver element exerts a traction force on said elongate strip.

Advantageously, said traction force is at a maximum when the device is first used and reduces on each actuation as the spring relaxes.

Advantageously, said spring is a traction spring of the coil spring type.

Advantageously, said receiver element includes a peripheral set of teeth that co-operates with said movable traction member.

Advantageously, at least one toothed wheel is interposed between said receiver element and said movable traction member.

Advantageously, said spring is fastened firstly to said movable traction member and secondly to a stationary portion of the device.

Advantageously, said movable traction member is a rotary disk that is provided with a peripheral set of teeth that co-operates with the peripheral set of teeth of the receiver element.

Advantageously, said spring is fastened to said rotary disk in the proximity of its peripheral edge.

Advantageously, said movable traction member is a notched rod that is provided with a set of teeth that co-operates with the peripheral set of teeth of the receiver element.

Advantageously, said spring is fastened to one end of said rod.

Advantageously, the displacement of said rod is guided by guide means.

Advantageously, said opening means comprise a needle that does not move relative to said body, a reservoir being displaced against said needle each time the device is actuated, said needle penetrating into said reservoir so as to empty it by means of an inhalation flow.

Advantageously, said opening means are controlled by the user inhaling, such that the reservoir is opened and emptied simultaneously by said inhalation flow.

These characteristics and advantages and others of the present invention appear more clearly from the following detailed description, given by way of non-limiting example, and with reference to the accompanying drawings, and in which.

Figure 1:
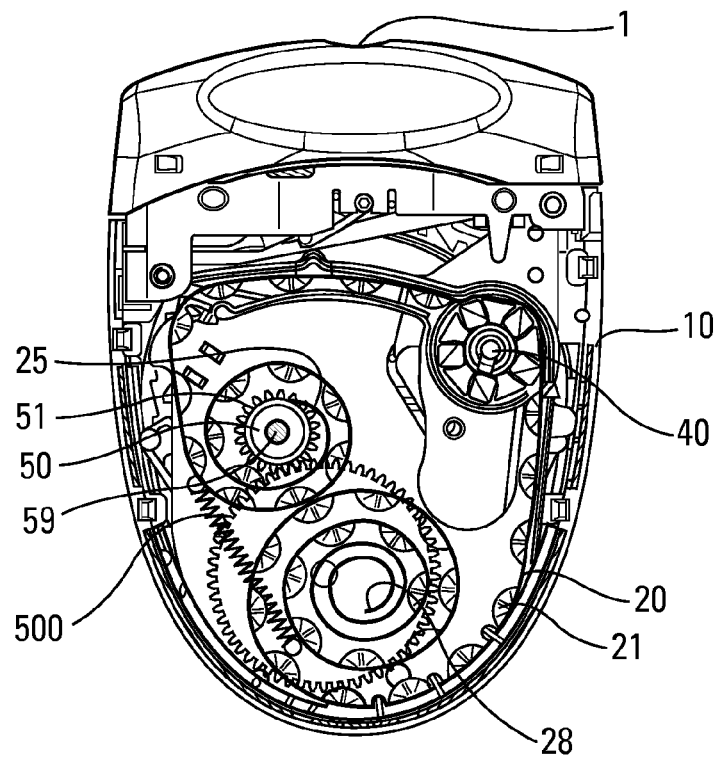
FIG. 1 is a cross-section view of a dispenser device in a first advantageous embodiment of the invention.

The figures show an advantageous embodiment of a dry-powder inhaler. The inhaler includes a body 10 on which there can be slidably mounted two cap-forming portions (not shown) that are adapted to be opened so as to open and load the device. The body 10 can be approximately rounded in shape, as shown in the figures, but it could be of any other appropriate shape. The body 10 includes a mouthpiece or inhaler endpiece 1 that defines a dispenser orifice through which the user inhales while the device is being actuated. The caps can be opened by pivoting about a common pivot axis, but any other opening means can be envisaged for opening the device. In a variant, the device could include a single cover instead of two.

Inside the body 10 there is provided a strip 20 of individual reservoirs 21, also known as blisters, said strip being made in the form of an elongate strip 20 on which the blisters 21 are disposed one behind another, in manner known per se. The blisters 21, preferably containing powder, are not shown in FIGS. 2 and 4, so as to avoid cluttering the drawings for the purpose of clarity. The blister strip 20 is advantageously constituted by a base layer or wall that forms the cavities receiving the doses of powder, and by a closure layer or wall that covers each of said blisters 21 in sealed manner. Before first use, the blister strip 20 can be rolled-up inside the body 10, preferably in a storage portion, and first strip displacement means 40, in particular rotary means, are provided for progressively unrolling the blister strip and for causing it to advance. Second displacement means, in particular means mounted to pivot on the body 10, are provided for bringing a respective blister or individual reservoir 21 into a dispensing position each time the device is actuated. The strip portion including the empty reservoirs is advantageously adapted to be rolled-up at another location of said body 10, preferably a reception portion, as described in greater detail below.

The inhaler includes reservoir opening means 30 preferably comprising perforator and/or cutter means for perforating and/or cutting the closure layer of the blisters. For example, the reservoir opening means advantageously comprise a needle 30 that is preferably stationary relative to the body 10, and against which a respective blister 21 is displaced on each actuation by the second displacement means. The blister is thus perforated by said needle which penetrates into said blister so as to expel the powder by means of the suction of the user inhaling.

The first displacement means 40 are adapted to cause the blister strip 20 to advance before and/or during and/or after each actuation of the device. The second displacement means are adapted to displace the reservoir to be emptied against said perforator and/or cutter means 30 during actuation. The second displacement means can be urged by a resilient element, such as a spring or any other equivalent resilient element, said resilient element being suitable for being prestressed while the device is being opened. The first displacement means preferably comprise an indexer wheel 40 that receives and guides the blisters. Turning the wheel 40 causes the blister strip 20 to advance. In a particular angular position, a given reservoir 21 is always in a position facing the opening means 30. The second displacement means can include a support element that is mounted to pivot about a pivot axis, said indexer wheel 40 being rotatably mounted on said support element.

An actuation cycle of the device can be as follows. While the device is being opened, the two cap-forming lateral portions are moved apart by pivoting on the body in order to open the device and thus pre-stress the device. In this position, the indexer wheel 40 cannot be displaced towards the needle 30, since the second displacement means are held by appropriate blocking means. Preferably, it is while the user is inhaling through the mouthpiece 1 that the blocking means are unblocked, thereby causing said indexer wheel 40 to be displaced towards the needle 30, and thereby causing a reservoir 21 to be opened.

In the embodiments shown, the reservoir 21 is displaced towards its open position so as to be opened by the needle 30 that does not move relative to the body 10. However, it can be envisaged that the needle could also be movable during the stage of opening the reservoir 21. For example, the needle could be displaced towards the reservoir 21 while the reservoir 21 is being displaced towards the needle. In another variant, it is also possible to envisage that the reservoir 21 and the needle are displaced in the same direction during actuation, the reservoir 21 being displaced more quickly in said direction, such that it comes into contact with the needle so as to be opened.

As explained above, it is desirable for the opening means to be actuated by the user inhaling. In order to trigger the reservoir opening means by inhalation, an inhalation trigger system is provided that advantageously comprises a unit (not shown) that is displaceable and/or deformable under the effect of inhalation, the unit being adapted to release the blocking means. The unit advantageously comprises a deformable air-chamber. Inhalation by the user causes said deformable air-chamber to deform, thereby making it possible to release said blocking means and to enable the second displacement means to be displaced, and therefore to enable a respective reservoir 21 to be displaced towards its opening position. The reservoir 21 is therefore opened only on inhalation, such that it is emptied simultaneously. Thus, there is no risk of any of the dose being lost between opening the reservoir and emptying it.

In a variant, other inhalation trigger means could also be used, e.g. using a pivotable valve flap that, while the user is inhaling, pivots under the effect of the suction created by the inhalation, with pivoting of the valve flap causing the blocking means blocking the movable support means to be released, thereby causing the reservoir to be displaced towards the opening means.

The inhaler further includes a dispenser or dispersion chamber (not shown) for receiving the dose of powder after a respective reservoir 21 has been opened. Advantageously, the dispenser chamber is provided with at least one bead (not shown) that is displaced inside said chamber during inhalation so as to improve the dispensing of the air and powder mixture after a reservoir 21 has been opened, in order to increase the effectiveness of the device.

It can be advantageous for the opening means 30, in particular the needle, to be formed directly on said dispenser chamber, e.g. at the end of a channel leading to said chamber.

After inhalation, when the user closes the device, all of the components return to their initial, rest positions. The device is thus ready for a new utilization cycle.

In an advantageous aspect of the inhaler, the individual reservoirs or blisters 21 are formed on an elongate strip 20 that, initially, is mainly stored in the form of a roll in a storage housing inside the body 10 of the device. Advantageously, the rolled-up blister strip 20 is held by inner walls of said storage housing without its rear end 28 (rear in the advancement direction of the blister strip 20) being fastened relative to said body 10, thereby enabling the blister-strip roll to be assembled more easily inside the device. The blister strip 20 is displaced by the user, advantageously by means of the indexer wheel 40 that advantageously presents at least one and preferably more recesses, each having a shape that corresponds to the shape of the blisters. Thus, when the indexer wheel 40 turns, it causes the blister strip 20 to advance. Naturally, in a variant or in additional manner, it is possible to use other means for advancing the blister strip, e.g. providing a profile on the longitudinal lateral edges of the blister strip, said profile being adapted to co-operate with appropriate drive means. In addition, holes formed along the lateral edges of the blister strip could also be used to cause the blister strip to advance by means of toothed wheels co-operating with said holes.

After opening one or more blisters, the blister-strip portion with the empty reservoirs must be suitable for being stored in easy and compact manner in the device, while avoiding any risk of blockage. Advantageously, the used blister strip is rolled-up automatically, once again forming a roll.

In the invention, the leading end 25 of the blister strip 20 is fastened to a rotatably-mounted receiver element 50. To ensure that the leading portion of the blister strip 20, namely the portion including the empty blisters, is rolled up properly in the reception portion, the rotary receiver element 50 is adapted to exert a traction force on the strip 20, in particular on its leading end 25. Thus, any risk is avoided of the strip being rolled up poorly, e.g. folding up concertina-like, etc., which would risk blocking the device. The traction force is exerted by a spring 500, preferably a coil spring, that urges said receiver element 50 to turn and thus pulls on the strip.

The figures show advantageous variant embodiments in which the receiver element 50 forms a cylinder that is rotatably mounted about a pivot pin 59.

In the invention, the rotary receiver element 50 includes a peripheral set of teeth 51 that co-operates with a movable traction member 510. The spring 500 is fastened firstly to said traction member 510 at 550 and secondly to a stationary portion of the device at 540. Thus, the spring exerts its traction force on said movable traction member 510 so as to displace it, a displacement of said movable traction member 510 causing the receiver element 50 to turn, and thus applying traction on the leading end 25 of the blister strip 20. This embodiment is advantageous in that it makes it possible to use a conventional traction spring that is simple to assemble, unlike a spiral spring that acts directly on the receiver element. Control of the traction force exerted by the receiver element 50 on the strip is also improved.

The spring 500 is stressed before first use or during assembly, and naturally, the maximum traction force exerted on the strip 20 is insufficient to tear, deform, or displace the strip 20 in the absence of actuation. Progressively, on each actuation, the spring relaxes on displacing the traction member 510, thereby causing the receiver element 50 to turn. The characteristics of the spring 500 are preferably selected such that it exerts a traction force until the last doses, but in certain applications, it may be sufficient for the traction force to be exerted only at the start of use, so as to guarantee a proper start of rolling-up for the strip portion with the empty reservoirs.

Figure 2:
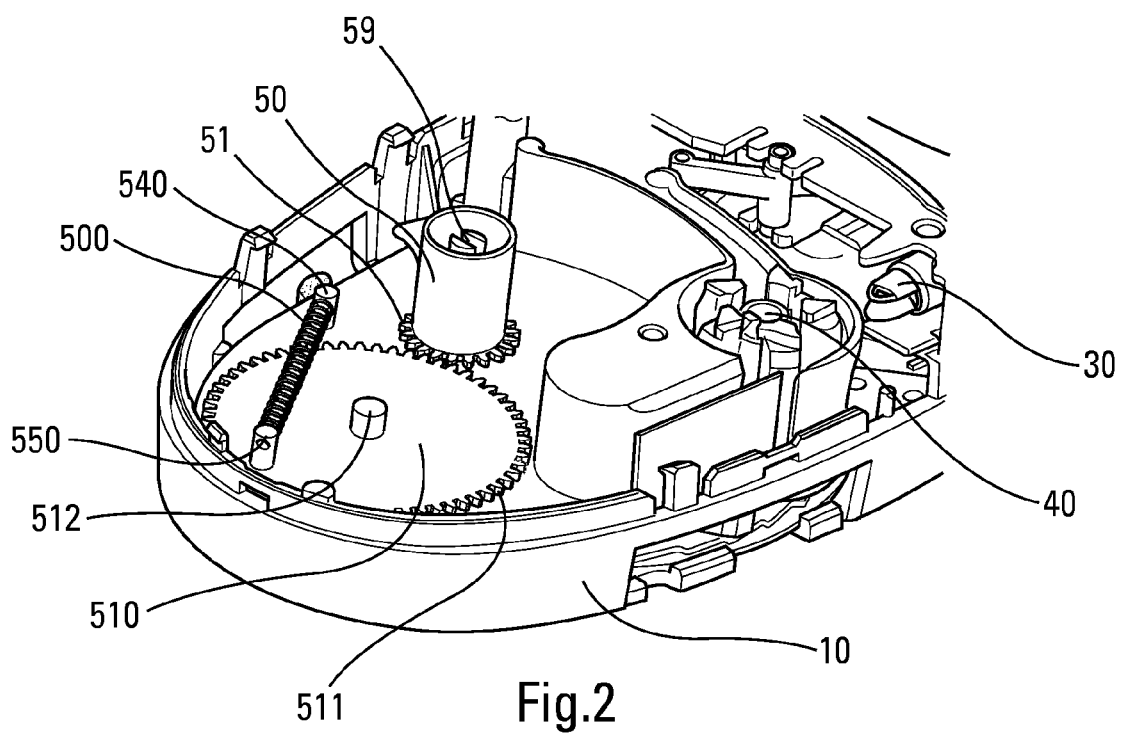
FIG. 2 is a diagrammatic and fragmentary perspective view of the FIG. 1 device.

FIGS. 1 and 2 show a first embodiment in which the movable traction member 510 is a rotary disk that is provided with a peripheral set of teeth 511 that co-operates with the peripheral set of teeth 51 of the receiver element 50. The spring 500 is fastened to a lug 550 of the rotary disk 510, which lug is formed in the proximity of its peripheral edge. Advantageously, the radial dimension of the rotary disk 510 is greater than the radial dimension of the receiver element so as to provide a maximum number of teeth in the peripheral set of teeth 511 of the disk 510. Even by optimizing the positioning of the spring 500, the arrangement in FIGS. 1 and 2 enables the rotary disk 510 to be displaced over less than a half turn. Optionally, one (or more) additional toothed wheel(s) may be provided between the receiver element 50 and the traction member 510, so as to reduce still further the degree to which said traction member 510 turns.

Figure 3:
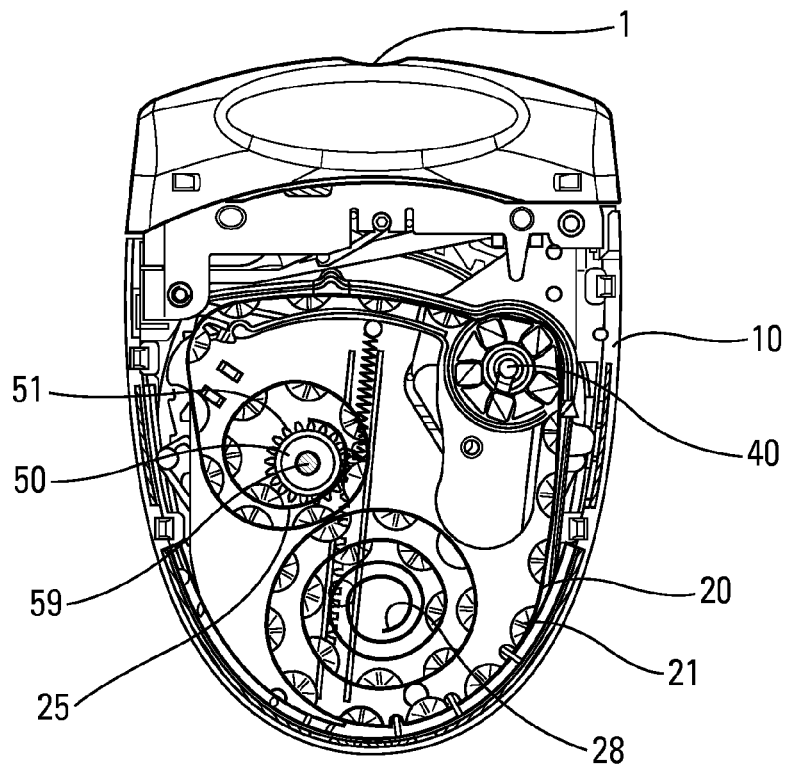
FIG. 3 is a view similar to the view in FIG. 1 of a second advantageous embodiment of the invention.
Figure 4:
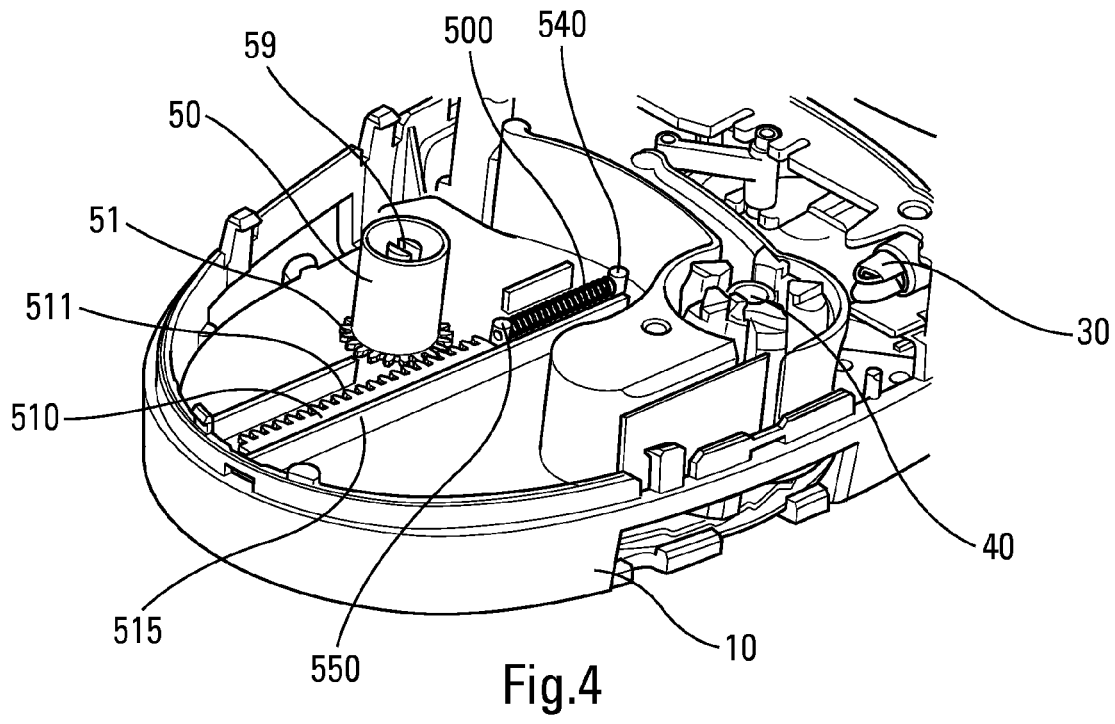
FIG. 4 is a diagrammatic and fragmentary perspective view of the FIG. 3 device.

FIGS. 3 and 4 show a second embodiment in which the movable traction member 510 is a notched rod of the rack type. The teeth 511 of said rod 510 co-operate with the set of teeth 51 of the receiver element 50. In this variant, the spring 500 is fastened to one end 550 of said rod and extends longitudinally therefrom. The stressed spring 500 thus pulls on said rod 510 that, on being displaced, causes the receiver element 50 to turn. Advantageously, guide means 515 are provided so as to guide the longitudinal displacement of the rod 510. Similar guide means may also be provided for the spring 500.

Other types of traction member could also be envisaged.

The traction force exerted by the rotary element 50 on the strip 20 is completely independent of the first displacement means, namely the indexer wheel 40 that causes the strip 20 to advance during each actuation. This makes it possible to guarantee that the traction force does not depend on the rolled-up diameter of the used blister strip, as would occur if the turning of the rotary receiver element 50 was correlated to the turning of the indexer wheel 40. It is also completely independent of the second displacement means, such that the invention avoids providing actuator means that are relatively complex in order to create traction force on the strip during actuation of the inhaler. This simplifies manufacture and assembly of the inhaler.

Advantageously, the receiver element 50 is disposed approximately at the center of the reception portion. The reception portion can include guide walls, in particular an external guide wall that is curved, e.g. cylindrical, and against which the blister strip 20 slides. An internal guide wall may also be provided at the inlet to the reception portion, and preferably extends approximately parallel to the external guide wall, so as to form a guide channel for the blister strip 20. The guide walls further facilitate proper rolling of the blister strip 20 onto the receiver element 50.

The present invention therefore makes it possible to provide a dry-powder inhaler that provides the following features:
- a plurality of individual doses of powder stored in individual sealed reservoirs, e.g. 30 or 60 doses stored on a rolled-up strip;
- the powder is released by perforation that is achieved by the user inhaling, the blister being perforated by means of an inhalation detector system that is coupled to a pre-stressed release system;
- appropriately-shaped drive means that are engaged with blisters so as to displace the blister strip on each actuation, and bring a new reservoir into a position in which it is to be opened by appropriate opening means;
- safe and reliable storage of the used portion of the strip, by being rolled onto a rotary element that is adapted to pull on the strip on each actuation, the traction being completely independent of the first displacement means, namely the indexer wheel that is used to cause the blister strip to advance.

Other features are also provided by the device of the invention as described above. It should be observed that the various features, even if they are shown as being provided simultaneously on the various embodiments of the inhaler, could be implemented separately. In particular, the inhalation trigger mechanism could be used regardless of the type of reservoir opening means, regardless of the use of a dose indicator, regardless of the way in which the individual reservoirs are arranged relative to one another, etc. The cocking means and the inhalation trigger system could be made in some other way. The same applies for other component parts of the device.

Various modifications may also be envisaged by a person skilled in the art, without going beyond the ambit of the present invention, as defined by the accompanying claims.

The invention claimed is:

1. A fluid dispenser device comprising a body, said device further comprising: an elongate flexible strip supporting a plurality of reservoirs, each containing a dose of fluid or powder; reservoir-opening means for opening a respective reservoir on each actuation, wherein said opening means comprise a needle that does not move and does not pivot relative to said body, a reservoir being displaced against said needle each time the device is actuated, said needle penetrating into said reservoir so as to empty the reservoir by means of an inhalation flow and said needle not moving and not pivoting relative to said body while penetrating into said reservoir; first rotating displacement means for causing said flexible strip to advance before and/or during and/or after each actuation, so as to bring a full reservoir into register with said reservoir-opening means; and second pivoting displacement means for displacing a full reservoir against said opening means each time the device is actuated, the leading end of said flexible strip, in the advance direction of said strip, being fastened to a rotary receiver element, wherein said receiver element includes a set of peripheral teeth that co-operates with a movable traction member, a stressed spring acting on said movable traction member so as to displace said movable traction member, the displacement of said movable traction member causing said receiver element to turn, such that said receiver element exerts a traction force on said elongate strip;

wherein said spring is a linear traction spring of the coil spring type.

2. A device according to claim 1, wherein said traction force is at a maximum when the device is first used and reduces on each actuation as the spring relaxes.

3. A device according to claim 1, wherein said receiver element includes a peripheral set of teeth that co-operates with said movable traction member.

4. A device according to claim 1, wherein at least one toothed wheel is interposed between said receiver element and said movable traction member.

5. A device according to claim 1, wherein said spring is fastened firstly to said movable traction member and secondly to a stationary portion of the device.

6. A device according to claim 1, wherein said movable traction member is a rotary disk that is provided with a peripheral set of teeth that co-operates with the peripheral set of teeth of the receiver element.

7. A device according to claim 6, wherein said spring is fastened to said rotary disk in the proximity of a peripheral edge of the disk.

8. A device according to claim 1, wherein said movable traction member is a notched rod that is provided with a set of teeth that co-operates with the peripheral set of teeth of the receiver element.

9. A device according to claim 8, wherein said spring is fastened to one end of said rod.

10. A device according to claim 8, wherein the displacement of said rod is guided by guide means.

11. A device according to claim 1, wherein said opening means are controlled by the user inhaling, such that the reservoir is opened and emptied simultaneously by said inhalation flow caused by inhaling by a user.

12. The device according to claim 1, wherein said linear traction spring is configured in the device to apply a spring force to displace said movable traction member through linear movement of said linear traction spring along a longitudinal axis of said linear traction spring.

* * * * *